Jan. 28, 1975 M. L. EFIRD Plant Pat. 3,676
AZALEA PLANT
Filed Aug. 6, 1973
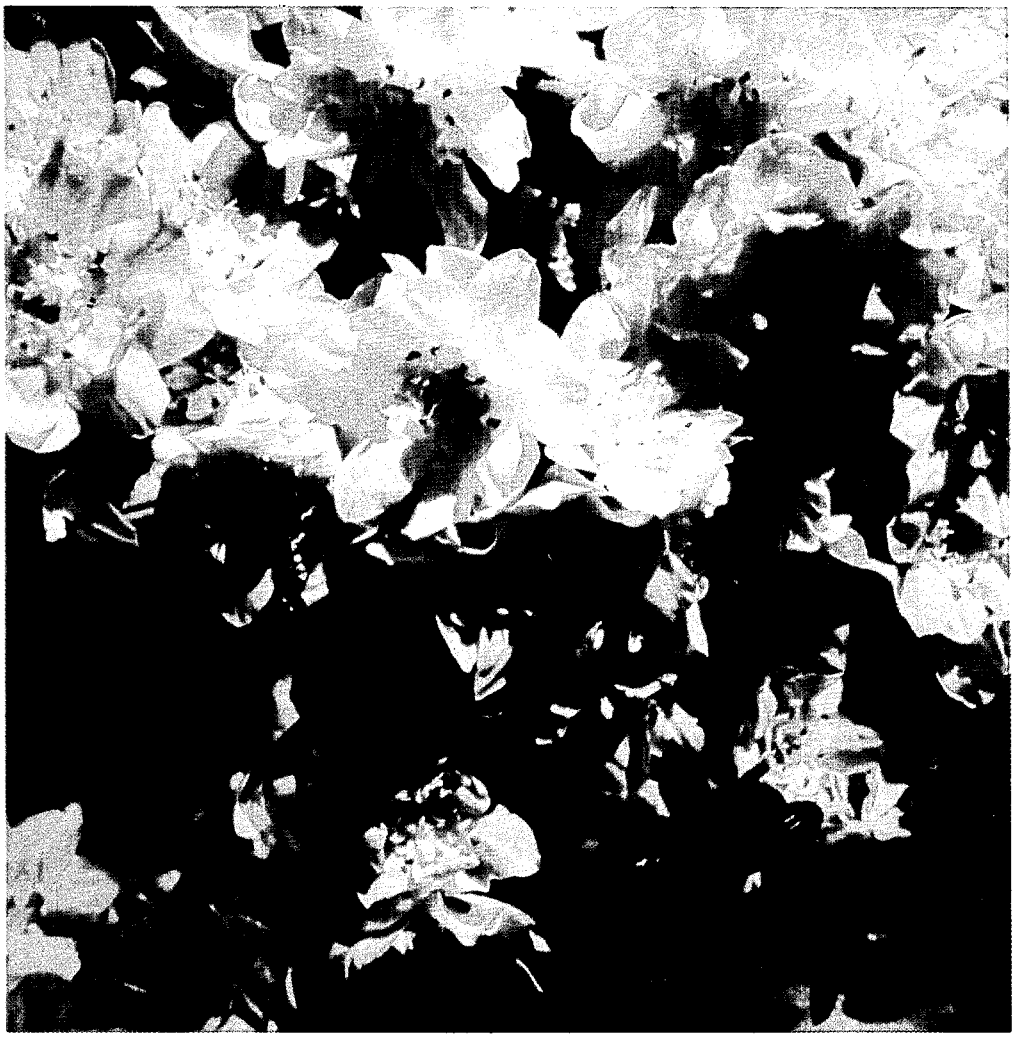

United States Patent Office

Plant Pat. 3,676

Patented Jan. 28, 1975

3,676

AZALEA PLANT

Maggie Lee Efird, Albermarle, N.C., assignor of a fractional part interest to Daniel J. Cagle, Seagrove, N.C.

Filed Aug. 6, 1973, Ser. No. 385,870

Int. Cl. A01h *5/00*

U.S. Cl. Plt.—55 1 Claim

The present invention relates to a new and distinct variety of Kurume azalea plant originating as a chance mutation from the Kurume azalea plant "Snow" in a cultivated area at applicant's nursery in Albemarle, N.C.

The principal object of the selection of the new variety was to produce an azalea plant having the appearance and characteristics of "Snow," with the exception that the flowers are of the white double hose-in-hose type as opposed to the single hose-in-hose type of "Snow."

The foregoing objective was attained by asexual propagation of the mutation by cuttings performed at applicant's nursery in Albemarle, N.C., showing that the plant reproduced true to form with the foregoing distinctive characteristics being transmitted through succeeding propagations. The accompanying drawings, forming a part hereof, show a typical plant of the new variety of azalea, the color of the latter being as nearly as it is reasonably possible to make the same in a color illustration of this character.

The following is a detailed description of the new variety of azalea plant, which I call "Snowball," color references being to the ordinary dictionary meaning of the terms.

THE PLANT

The present azalea plant is identical to the Kurume azalea "Snow," even to the persistence of the old flowers after fading. More specifically, the plant is of a dense, upright character having a medium height to six feet. The summer leaves are evergreen, oblanceolate, and are one inch to one and a half inches long and one-half to three-fourths inches wide.

The plant is resistant to diseases and insects as observed in Zones 7 and 8 as shown in the Plant Hardiness Zone Map, Misc. Publication #814 Agricultural Research Service, U.S.D.A. No winter damage or seasonable damage to the plants has been observed during the last five years, during which the plants have been exposed to −3° for three nights and with ground frozen for five weeks.

THE FLOWER

The flowers of the present plant are of a double hose-in-hose structure and are from one and a half to two inches across with 30 petals. The stamens are transformed to small petal-like structures with five to fifteen small light tan filament remains at the ends thereof. The flowers are white in color with a faint chartreuse coloring at the base of the petals and also at the exterior base of the corolla tube similar to the coloring of "Snow."

The flowers of the azalea plant differ from those of the Pericat azalea "Gardenia Supreme" in that the flowers lack the violet red blotching in the throat observable in "Gardenia Supreme." Also, the present plant is more compact and flowers earlier.

I claim:

1. A new and distinct variety of azalea plant of the hardy evergreen type, substantially as herein shown and described, characterized particularly by white double hose-in-hose flowers.

No references cited.

ROBERT E. BAGWILL, Primary Examiner